(12) United States Patent
Ready et al.

(10) Patent No.: US 8,774,890 B2
(45) Date of Patent: Jul. 8, 2014

(54) ELECTRODE ARRAYS AND METHODS OF MAKING AND USING SAME

(75) Inventors: William Judson Ready, Atlanta, GA (US); Kirsten LeAnn Kepple, Canton, OH (US)

(73) Assignee: Georgia Tech Research Corporation, Atlanta, GA (US)

( * ) Notice: Subject to any disclaimer, the term of this patent is extended or adjusted under 35 U.S.C. 154(b) by 644 days.

(21) Appl. No.: 12/935,122

(22) PCT Filed: Mar. 30, 2009

(86) PCT No.: PCT/US2009/038849
§ 371 (c)(1),
(2), (4) Date: Sep. 28, 2010

(87) PCT Pub. No.: WO2010/008627
PCT Pub. Date: Jan. 21, 2010

(65) Prior Publication Data
US 2011/0082413 A1    Apr. 7, 2011

Related U.S. Application Data

(60) Provisional application No. 61/040,365, filed on Mar. 28, 2008.

(51) Int. Cl.
*A61B 5/04* (2006.01)
*A61N 1/30* (2006.01)

(52) U.S. Cl.
USPC .............. 600/377; 604/21; 600/393; 607/116

(58) Field of Classification Search
USPC ............ 600/377, 372, 373, 393, 395; 604/21; 607/116
See application file for complete search history.

(56) References Cited

U.S. PATENT DOCUMENTS 6,689,117 B2    2/2004  Sweeney et al.
6,755,530 B1 *  6/2004  Loftus et al. .................. 351/246

(Continued)

OTHER PUBLICATIONS

Parthangal, et al. "A generic process of growing aligned carbon nanotube arrays on metals and metal alloys" Nanotechnology 18(18) 185605 (2007).*

(Continued)

*Primary Examiner* — Lee S Cohen
*Assistant Examiner* — Erin M Cardinal
(74) *Attorney, Agent, or Firm* — Troutman Sanders LLP; Ryan A. Schneider; Troy S. Kleckley (57) ABSTRACT

Described herein are improved electrode array devices and improved active agent delivery devices. Further described are methods of making and using the improved devices. An improved electrode array device includes a substrate and a plurality of probes disposed on the substrate, wherein the probes are formed from a plurality of aligned carbon nanotubes that are not encapsulated by a structure-providing material. An active agent delivery device includes a substrate having an aperture therein, an active agent delivery member disposed on a first surface of the substrate and having an aperture therein, and an active agent chamber disposed on a second surface of the substrate configured to deliver an active agent through the aperture of the substrate and the aperture of the active agent delivery member.

16 Claims, 6 Drawing Sheets

(56) References Cited

U.S. PATENT DOCUMENTS

| | | |
|---|---|---|
| 2004/0186459 A1 | 9/2004 | Shur et al. |
| 2006/0129043 A1* | 6/2006 | Ben-Jacob et al. ............ 600/373 |
| 2006/0263839 A1* | 11/2006 | Ward et al. ...................... 435/14 |
| 2007/0187840 A1 | 8/2007 | Dell'Acqua-Bellavitis et al. |
| 2008/0177363 A1* | 7/2008 | Schouenborg ................ 607/116 |
| 2010/0196446 A1* | 8/2010 | Gharib et al. ................. 424/443 |
| 2010/0249877 A1* | 9/2010 | Naughton ....................... 607/54 |

OTHER PUBLICATIONS

International Search Report and Written Opinion dated Dec. 10, 2009 for corresponding PCT Application No. PCT/US2009/038849.

Wang, K. et al., "Fabrication of Carbon Nanotube Protruding Electrode Array for a Retinal Prosthesis", Proceedings of SPIE, vol. 5718, pp. 22-29, 2005, Bellingham, WA.

\* cited by examiner

ELECTRODE ARRAYS AND METHODS OF MAKING AND USING SAME

CROSS-REFERENCE TO RELATED APPLICATIONS

This application is a United States National Stage Application of International Patent Application Ser. No. PCT/US2009/038849, filed 30 Mar. 2009, and entitled "Electrode Arrays and Methods of Making and Using Same," which claimed the benefit of U.S. Provisional Patent Application Ser. No. 61/040,365, filed 28 Mar. 2008, which are incorporated herein by reference in their entireties as if fully set forth below.

TECHNICAL FIELD

The various embodiments of the present invention relate generally to electrode arrays, and more particularly, to carbon nanotube-containing electrode arrays, and to methods of making and using such devices.

BACKGROUND

Electrode arrays, having a plurality of electrode probes or shanks, are widely used in biological applications, for example, to stimulate and/or record electrical activity in cells or tissues. By way of illustration, when the cells in nervous tissue (i.e., neurons and neuroglia) or muscle tissue (i.e., muscle cells) are excited, a current is generated. This current results in a change in voltage both inside and outside of the cells. Thus, an electrode array can be used to monitor the changes in voltage and/or to provide a voltage stimulus for the purposes of research, diagnosis, treatment or therapy, and the like.

Many electrode array devices suffer from poor biocompatibility. As part of the body's immunological response to a recognized foreign body, implanted electrode array devices can experience a biofouling process in which local cells surround the probes of the electrode array device and ultimately wall off the implanted device from the body. For example, within hours of implantation of an electrode array device for neural studies, an increased population of astrocytes and glial cells can surround the individual probes of the array. These microglia can then initiate inflammation, and the process of phagocytosis of the foreign material begins. Over time, the astrocytes and microglia begin to accumulate, forming a sheath surrounding the probes of the electrode array that extends tens of micrometers around the device.

As a result of such inflammation and biofouling processes, electrode array devices often must be removed and the same (or another) array must be implanted in another location. This cycle of chronic implantation and removal can result in inflammation, cell loss, scar tissue formation, and the like. Continuing the example of the electrode array device for neural studies described above, chronic implantation and removal of such devices has been shown to lead to neuron loss, axon length reduction, neurodegeneration, and glial scarring.

Accordingly, there remains a need for improved electrode array devices for biological applications. It would be particularly advantageous if the improved devices reduced or eliminated adverse immunological reactions thereto. Such improved electrode array devices would be more effective and have longer service lifetimes.

It is to the provision of such electrode array devices that some of the various embodiments of the present invention are directed.

BRIEF SUMMARY

The various embodiments of the present invention provide improved electrode array devices, improved active agent delivery devices, and methods of making and using such devices.

An electrode array device according to some embodiments of the present invention includes a substrate and a plurality of probes disposed on the substrate. Each probe of the plurality of probes can include a plurality of aligned carbon nanotubes. The plurality of aligned carbon nanotubes are not encapsulated by a structure-providing material, such as a polymeric matrix.

The electrode array device can also include a plurality of electrical contacts. Each electrical contact can be disposed between a probe and the substrate. The electrode array device can also include a processing component that is in electrical communication with at least one of the probes.

In some situations, each probe is electrically isolated from one another. The carbon nanotubes or each probe can be functionalized to increase the density of the carbon nanotubes within that probe. For example, the carbon nanotubes can be functionalized with poly-L-lysine. Alternatively, the carbon nanotubes can be functionalized with a laminin.

According to other embodiments of the present invention, an electrode array device includes a substrate and a plurality of probes disposed on the substrate. In some cases, each probe of the plurality of probes consists of a plurality of vertically aligned carbon nanotubes.

According to some embodiments of the present invention, an active agent delivery device can include a substrate having an aperture therein and an active agent delivery member disposed on a surface of the substrate and having an aperture therein. The active agent delivery member can be formed from a plurality of aligned carbon nanotubes. The aperture of the active agent delivery member and the aperture of the substrate can be substantially coaxial. The active agent delivery device can also include means for delivering an active agent through the aperture of the substrate and the aperture of the active agent delivery member.

An active agent delivery device, according to other embodiments of the present invention, can include a substrate having an aperture therein and an active agent delivery member disposed on a first surface of the substrate. The active agent delivery member can have an aperture therein. The active agent delivery member can be formed from a plurality of aligned carbon nanotubes. The aperture of the active agent delivery member and the aperture of the substrate can be substantially coaxial. The active agent delivery device can also include an active agent chamber disposed on a second surface of the substrate. The active agent chamber can be configured to deliver an active agent through the aperture of the substrate and the aperture of the active agent delivery member.

The active agent delivery device can include a processing component in electrical communication with the active agent chamber and/or the active agent delivery member.

The active agent delivery device can also include an electrical contact that is disposed between at least a portion of the active agent delivery member and at least a portion of the substrate.

Yet another active agent delivery device can include a substrate having a plurality of apertures therein and a plurality of active agent delivery members disposed on a first surface of the substrate. Each active agent delivery member of the plurality of active agent delivery members can have an aperture therein. Each active agent delivery member of the plurality of active agent delivery members can include a plurality of aligned carbon nanotubes. Each aperture of an active agent delivery member can be substantially coaxial with an aperture of the substrate. The active agent delivery device can further include an active agent chamber disposed on a second surface of the substrate configured to deliver an active agent through at least one aperture of the substrate and at least one active agent delivery member aperture.

Other aspects and features of embodiments of the present invention will become apparent to those of ordinary skill in the art, upon reviewing the following detailed description in conjunction with the accompanying figures.

BRIEF DESCRIPTION OF THE DRAWINGS

FIG. 6($a$) is a scanning electron microscope image of an array of carbon nanotube electrodes, after implantation, in accordance with the data in EXAMPLE 2.

FIG. 6($b$) is a scanning electron microscope image of a carbon nanotube electrode, after implantation, in accordance with the data in EXAMPLE 2.

FIG. 9($a$) is a scanning electron microscope image of an aperture in a silicon wafer in accordance with the data in EXAMPLE 3.

FIG. 9($b$) is a scanning electron microscope image of a carbon nanotube-containing active agent delivery member in accordance with the data in EXAMPLE 3.

DETAILED DESCRIPTION

Referring now to the figures, wherein like reference numerals represent like parts throughout the several views, exemplary embodiments of the present invention will be described in detail. Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," "primary," "secondary," "top," "bottom," "distal," "proximal," and the like, do not denote any order, quantity, or importance, but rather are used to distinguish one element from another. Further, the terms "a", "an", and "the" do not denote a limitation of quantity, but rather denote the presence of "at least one" of the referenced item.

As stated above, various embodiments of the present invention are directed to improved electrode array devices. The improved electrode array devices described herein are so-called "microelectrode arrays." Other embodiments of the present invention are directed to improved active agent delivery devices. The electrode array devices and active agent delivery devices are beneficial because their probes and active agent deliver members, respectively, are of such a small size that the body either does not recognize them as a foreign object to which an immunological response is necessary or has a delayed response to them. The improved devices described herein make use of a plurality of vertically aligned carbon nanotubes (CNTs) as the probes or active agent delivery members, as will be described in more detail below.

As used herein, the term "aligned" encompasses items having at least a portion of a dimension (e.g., length, width, height, or the like) being either parallel to each other or within about 15 degrees of being parallel to one another if projected infinitely into space. Thus, two CNTs that do not directly contact each other, but would contact each other if the CNTs were infinitely long, and the angle formed between them is less than or equal to about 15 degrees, are considered aligned for the purposes of this disclosure. When a number of items are described herein as being aligned, then at least 70 percent of the items are aligned with one another. Thus, in referring to a plurality of CNTs being vertically aligned, it is intended that at least a portion of the length (i.e., the axis perpendicular to the diameter of the CNT) of at least 70 percent of the CNTs in the plurality are aligned. For example, when a plurality of vertically aligned CNTs are not linear and/or bundle together to form so-called "ropes," then a portion of the lengths (or the entire lengths) of at least 70 percent of the CNTs are either parallel or within about 15 degrees of being parallel to one another.

Figure 1:
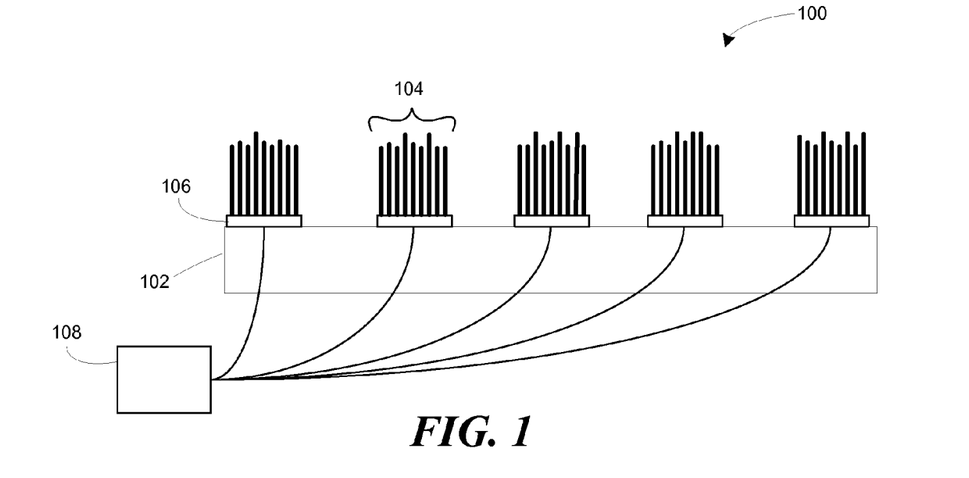
FIG. 1 is a schematic illustration of a carbon nanotube-containing electrode array device in accordance with some embodiments of the present invention.

A cross-section of an electrode array device, according to some embodiments of the present invention, is shown in FIG. 1. The electrode array device, which is designated by reference numeral 100, generally includes a substrate 102 and a plurality of probes or shanks 104 disposed on at least a portion of the substrate 102.

Within the electrode array device 100, there is no limitation on the composition or material from which the substrate 102 is formed. When the plurality of probes 104 are intended to be electrically isolated from one another so as to provide each probe 104 with the ability to discretely measure and/or stimulate a specific location of the bio-environment in which the electrode array device 100 is implanted for in vivo applications (or to which the electrode array device 100 is contacted for in vitro applications), the substrate 102 must be formed from an insulating or dielectric material. This is to prevent the possibility of a short circuit between individual probes 104 of the electrode array device 100.

If the plurality of probes 104 are designed to provide a uniform stimulus and/or to take a single measurement across the entire electrode array device, then the substrate 102 does not need to be formed from an insulating material. This configuration will be described in more detail with reference to FIG. 2 below.

Each probe 104 of the plurality of probes comprises a plurality of vertically aligned CNTs that project away from the substrate 102. The probes 104 can be directly or indirectly (i.e., via an intermediate layer of material) connected to the substrate 102. In addition, the probes 104 can be oriented perpendicular to, or slanted at any angle with respect to, the substrate 102.

The CNTs that are used to make the probes 104 of the electrode array device 100 can be any type of carbon nanotube, including single wall nanotubes (SWNTs), multi-wall carbon nanotubes (MWNTs), or a combination of both types of carbon nanotubes. Additional details regarding the CNTs will be provided below in describing the manufacture of the electrode array device 100.

There is no particular limitation on the shape of the probes 104. The probes 104 can be identical to one another, or can have different shapes. Thus, the plurality of vertically aligned CNTs of a probe 104 can have the shape of a circle, triangle, square, rectangle, pentagon, a cross, a star, a torus or donut, any other polygon whether solid or hollow (e.g., like donut), or any other shape.

There is no particular limitation on the height of the CNTs of the probes 104. The probes 104 can have identical heights, or they can have different heights. For example, it may desirable to have probes 104 of different heights so that each probe 104 can measure electrical activity or stimulate not only different lateral areas but different depths within the bio-environment in which the electrode array device 100 is implanted for in vivo applications (or to which the electrode array device 100 is contacted for in vitro applications).

When the pressure necessary to penetrate into a particular type of tissue is high, the CNTs can be arranged to provide the probes 104 with a quality of "sharpness." That is, there can be a gradient in the height of the CNTs such that those in the center of the plurality of vertically aligned CNTs are taller than those at the periphery of the plurality of vertically aligned CNTs so as to mimic the tip of a sharp pencil. In other situations, the gradient in the height of the CNTs can be created to provide a saw-toothed or serrated profile. Alternatively, the overall shape of the probes 104 can be used to provide similar features. For example, the CNTs can be arranged to have a star-shape, wherein the CNTs of each side or leg of the star have a gradient in the height of the CNTs such that those in the center of the side or leg are taller than those at the periphery of the side or leg of the star. Other arrangements of the CNTs in each probe 104 can be created to provide a quality of sharpness as will be understood by those skilled in the art to which this disclosure pertains.

The longest lateral cross-sectional dimension of the probes 104 is less than about 50 micrometers. As used herein "lateral cross-sectional dimension" refers to a particular dimension of a probe 104 that is parallel to the surface of the substrate 102. Thus, to clarify, when a probe 104 is circular, the longest lateral cross-sectional dimension is its diameter; when a probe 104 is square-shaped, the longest lateral cross-sectional dimension is the diagonal between two opposite corners; and when a probe 104 is star-shaped, the longest lateral cross-sectional dimension is the line between any two opposing legs or sides of the star. Without intending to be bound by theory, it is believed that the body does not recognize or has difficulty recognizing foreign objects that are smaller than about 50 micrometers. Thus, because the probes 104 have dimensions that are smaller than this threshold size, they are less likely to be susceptible to any biofouling or otherwise adverse reactions.

The minimum spacing between individual probes 104 should be sufficiently large that electrical isolation can be maintained therebetween. Also, the probes 104 should be sufficiently far apart from one another that the body's immunological response is not triggered. Otherwise, there is no limitation on the number and spacing of probes 104 on a particular substrate 102.

The electrode array device 100 can further include an (i.e., at least one) optional processing component or unit 108. The optional processing component 108 is configured to record any voltage changes detected by the individual probes 104 and/or provide stimulus voltages to the individual probes 104. The processing component 108 can include a voltage source, an amplifier, a multi-channel switch, a computing device, signal processing circuitry, signal processing software or algorithms, or combinations of two or more of the foregoing. The individual devices of the processing component 108 and the arrangement thereof will be understood by those skilled in the art to which this disclosure pertains.

Because the plurality of probes 104 in the electrode array device 100 of FIG. 1 are electrically isolated from one another, each of the probes 104 independently must be in electrical communication with the processing component 108.

In order for each probe 104 to be electrically isolated from one another, the electrode array device 100 must have an electrical contact 106 for each probe 104. The electrical contact 106 can be a conducting layer interposed between the substrate 102 and the probe 104.

During operation of the electrode array device 100, the electrode array device 100 is implanted in, or contacted with, the bio-environment of interest. For illustrative convenience only, and with no intention to be limited thereto, reference will be made to nervous tissue or muscle tissue as the bio-environment of interest. When the electrode array device 100 is used to measure electrical activity, each individual probe 104 will transduce any change in voltage from the muscle tissue or nervous tissue environment (e.g., a twitch in muscle cells, an action potential in neurons, or the like) caused by ion conduction into an electric current. These electric currents are then measured by the processing component 106 for subsequent processing or analysis. When the electrode array device 100 is used to provide electrical activity for stimulation, the processing component 106 will provide an electric current to a specific probe(s) 104. The probe 104 will transduce the electric current into an ionic current through the muscle or nervous tissue. The ionic current then triggers the voltage-gated ion channels on the membranes of the excitable cells, causing the cells to depolarize and trigger either an action potential if it a nervous cell or a twitch if it is a muscle cell.

An advantage of using a plurality of vertically aligned CNTs as a probe 104 for the electrode array device 100 is that the probes 104 can have dimensions that are significantly smaller than existing electrode array devices. The high conductivity of CNTs allows for greater sensitivity than other probe compositions; and the high Young's modulus of the CNTs allows for greater mechanical stability than other probe compositions. As a result, the probes 104 can be made to have significantly smaller lateral cross-sectional dimensions and shorter lengths. For example, in some cases, the probes 104 have longest lateral cross-sectional dimensions that are less than or equal to about 20 micrometers. In certain cases, these dimensions can be less than or equal to about 10 micrometers. In situations where greater sensitivity is required, larger probes should be selected.

Another advantage of using a plurality of vertically aligned CNTs as a probe 104 for the electrode array device 100 is that the electrical activity is not measured or stimulated from any one point, but is spread across many single nanotubes. Thus, in contrast to existing electrode array devices where a probe consists of a single element or member, a probe 104 within the electrode array device 100 of the present invention does not fail simply because a single CNT fails (e.g., because of biofouling, improper positioning, or the like) to measure or stimulate electrical activity.

A process for making the electrode array device 100 includes first providing a substrate 102 on which the probes 104 can be disposed. Next, the electrical contacts 106 can be disposed on the substrate 102. This can be accomplished using any known technique for doing so. For example, the electrical contacts 106 can be pre-fabricated, and can be fastened (e.g., mechanically or chemically) to the substrate 102. Alternatively, the electrical contacts 106 can be fabricated directly on the substrate 102 using any known fabrication technique. Examples of such techniques include physical vapor deposition and all of the variants thereof, chemical vapor deposition and all of the variants thereof, electroless or electrolytic plating, wet chemical methods (e.g., sol-gel, chemical surface modifications, or other like method), sputtering and all of the variants thereof, ablation deposition and all of the variants thereof, molecular beam epitaxy and all of the variants thereof, photolithography, thermal surface modifications, and the like.

Mechanisms for rendering the electrical contacts 106 in electrical communication with the processing component 108 can be implemented. For example, individual electrical leads are coupled to the electrical contacts 106. The electrical leads can be disposed on the substrate, through the substrate, or the like. This can be accomplished using any known fabrication technique either before, after, or at the same time the electrical contacts 106 are disposed on the substrate.

After the electrical contacts 106 have been disposed on the substrate 102, the pluralities of vertically aligned CNTs can be created on the electrical contacts 106.

Once again, the CNTs that are used to make the probes 104 of the electrode array device 100 can be any type of carbon nanotube, including SWNTs, MWNTs, or a combination of both types of carbon nanotubes. The CNTs can be made from any known means, including, but not limited to, chemical vapor deposition and all of its variations (e.g., catalytic chemical vapor deposition using carbon-containing feedstocks and/or metal catalyst particles, plasma-enhanced chemical vapor deposition, thermally-enhanced chemical vapor deposition, and the like) or any other method for synthesizing carbon nanotubes on a surface.

The CNTs can also optionally include non-carbon elements in the backbone. For example, elements such as boron, nitrogen, sulfur, silicon, or the like, can be included in the backbone of the CNTs depending on the particular application for the electrode array device 100 formed therefrom.

The average diameter of the CNTs can be about 0.5 nanometers (nm) to about 75 nm. In some situations, it is desirable to use nanotubes having an average diameter of less than or equal to about 10 nm. The average length of the nanotubes can be greater than or equal to about 10 nm. For example, nanotubes having lengths on the order of millimeters or even centimeters could be used. In certain situations, however, the height of the nanotubes is less than about 50 micrometers.

It is desirable for the CNTs to have a purity of at least 95 percent (%), and preferably at least 99%, in order to minimize the potential for adverse affects caused by impurities within the CNT sample. Thus, the CNTs can optionally be purified to remove non-nanotube carbon, such as amorphous carbon, and metallic catalyst residues.

Purification can be achieved by any known means. Procedures for purification of carbon nanotubes (while on the electrical contacts 106) are well known to those skilled in the art to which this disclosure pertains. The optionally purified CNTs can also be dried. Similarly, procedures for drying CNTs (while on the electrical contacts 106) are well known to those skilled in the art to which this disclosure pertains.

Depending on the particular application for the electrode array device 100 formed therefrom, the CNTs can be optionally derivatized on their ends and/or sides with a functional group. These functional groups can include an alkyl; acyl; aryl; aralkyl; halogen; substituted or unsubstituted thiol; substituted or unsubstituted amino; hydroxyl; an OR' wherein R' can include an alkyl, acyl, aryl, aralkyl, substituted or unsubstituted amino, substituted or unsubstituted thiol, and halogen; a linear or cyclic carbon chain optionally interrupted with one or more heteroatom, and optionally substituted with one or more =O, or =S, hydroxyl, aminoalkyl group, amino acid, or a peptide; an amino acid (e.g., lysine, L-lysine, or modified lysine) or polymer thereof; or a laminin or polymer thereof. The extent of the substitution can be tailored to achieve the desired electronic or chemical effect, as would be understood to those skilled in the art to which this disclosure pertains. By way of one example, the number of carbon atoms in the alkyl, acyl, aryl, aralkyl groups can be in the range of 1 to about 30.

Also depending on the particular application for the electrode array device 100, the CNTs can be optionally treated (e.g., with an acid or other chemical) so as to alter their lengths.

After the CNTs have been disposed on the electrical contacts 106, the optional processing component 108 can be connected to the appropriate leads. The electrode 100 is then complete and is ready for use.

By way of example, one process for preparing an electrode array device 100 involves first providing a silicon wafer as the substrate 102. A thin film of $SiO_2$, which serves to render the substrate an insulator, is thermally grown on the top side of the substrate 102. The top surface of the substrate 102 (i.e., the one containing the $SiO_2$ film) is then patterned with a photo-resist using photolithography. The pattern corresponds to the locations of the pluralities of the electrical contacts 106 and, optionally, the electrical leads for coupling the electrical contacts 106 with the processing component 108.

A thin layer of chromium (Cr), copper (Cu), or other conductive material is subsequently deposited on the substrate 102 by electron beam evaporation. The portions of the thin film that are directly in contact with the substrate 102 act as the electrical contacts 106 and, optionally, the electrical leads. If the electrical leads are indeed made in this fashion, they are then patterned with a photoresist using photolithography. The apertures in this pattern correspond only to the locations of the pluralities of CNTs to be grown (which are directly on at least a portion of the electrical contacts 106).

The apertures allow for a line-of-sight deposition path for the deposition of an iron (Fe) catalyst layer directly on the electrical contacts 106. This will ensure that an ohmic connection exists between the probes 104 and the electrical contacts 106. The photo-resist and excess Fe is removed via a standard liftoff process making use of sonication in acetone. The CNTs are grown using catalyzed pyrolytic decomposition of hydrocarbon gases in a chemical vapor deposition chamber. In this case, the electrode array device 100 includes Fe catalyst particles between the pluralities of vertically aligned CNTs and the electrical contacts 106.

It is also possible for the Fe catalyst particles to serve as the electrical contacts 106. In these situations, the $SiO_2$ film of the substrate 102 is only patterned once. This pattern corresponds to the locations of the Fe catalyst layer to be grown. After the CNTs are grown on the Fe catalyst particles, the electrical leads are fabricated. These can be made by selectively plating portions of the substrate 102 corresponding to the leads themselves. Alternatively, electrical leads, in the form of nanowires or other like structure, can be deposited directly on the substrate 102.

The CNTs can be functionalized, for example, by dipping them in a solution of the functionalizing agent. If there is concern about damage to the other components of the electrode array device, then an additional photoresist layer can be created and removed to protect the other components during the functionalization step.

Once the probes 104, electrical contacts 106 and electrical leads are prepared on the substrate 102, the optional processing component 108 can be connected to the electrical leads.

Figure 2:
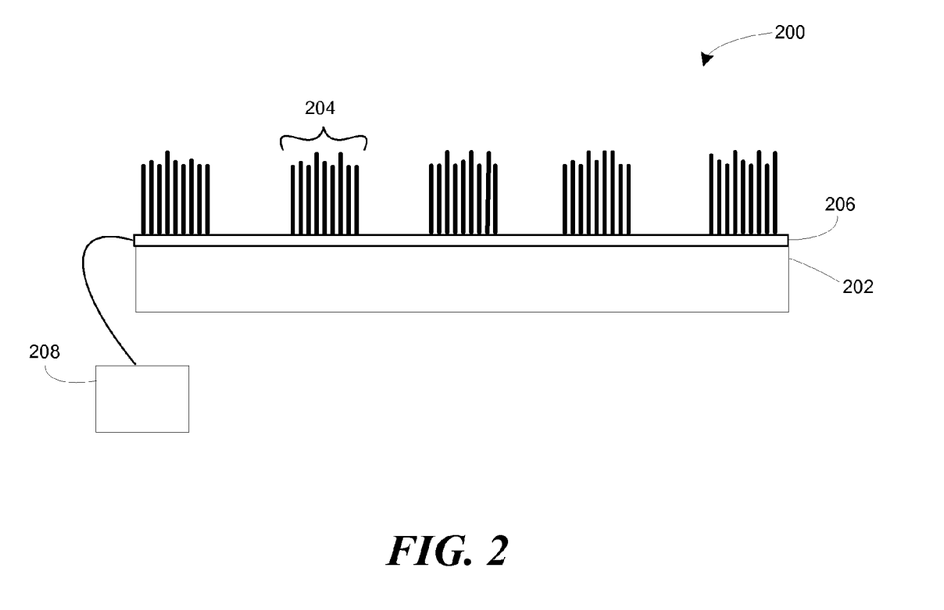
FIG. 2 is a schematic illustration of a carbon nanotube-containing electrode array device in accordance with other embodiments of the present invention.

Another improved electrode array device, according to some embodiments of the present invention, is shown in FIG. 2 and is generally designated by reference numeral 200. The electrode array device 200 comprises a substrate 202, a plurality of probes 204, and an optional processing component 208 exactly as described above for the electrode array device 100 of FIG. 1. Probes 204 are identical to probes 104 of the electrode array device 100 of FIG. 1, with the exception that they are not electrically insulated from one another. Thus, electrode array device 200 is designed to provide a uniform stimulus and/or to take a single measurement across the entire electrode array device 200.

Since the plurality of probes 204 are not electrically insulated from one another, the substrate 202 does not need to be formed from an insulating material. When the substrate 202 is formed from a conductive material, it can be in electrical communication with the optional processing component 208. If, however, the substrate 202 is formed from an insulating material, then the electrode array device 200 can further include an optional electronic contact 206. In these situations, which is shown in FIG. 2, the optional electronic contact can be in electrical communication with the optional processing component 208.

The electrode array device 200 of FIG. 2 can be fabricated exactly as described for the electrode array device 100 of FIG. 1, with the exception that a single electronic contact 206 can be prepared (if necessary) instead of a plurality of electrical contacts 106. If these are not needed, then the probes 204 can be disposed directly on the substrate 202.

Again, this type of electrode array device 200 is beneficial in situations where a single measurement and/or a uniform level of electric stimulation is desired. It should, however, be understood to those skilled in the art to which this disclosure pertains that an electrode array device can be prepared where a portion of the probes are electrically insulated from one another while another portion of the probes are not electrically insulated from one another. This hybrid-type electrical array device, while encompassed by the various embodiments of the present invention, is not illustrated in order to minimize redundancy. Specifically, such a device can be illustrated by merging the devices of FIGS. 1 and 2.

Figure 3:
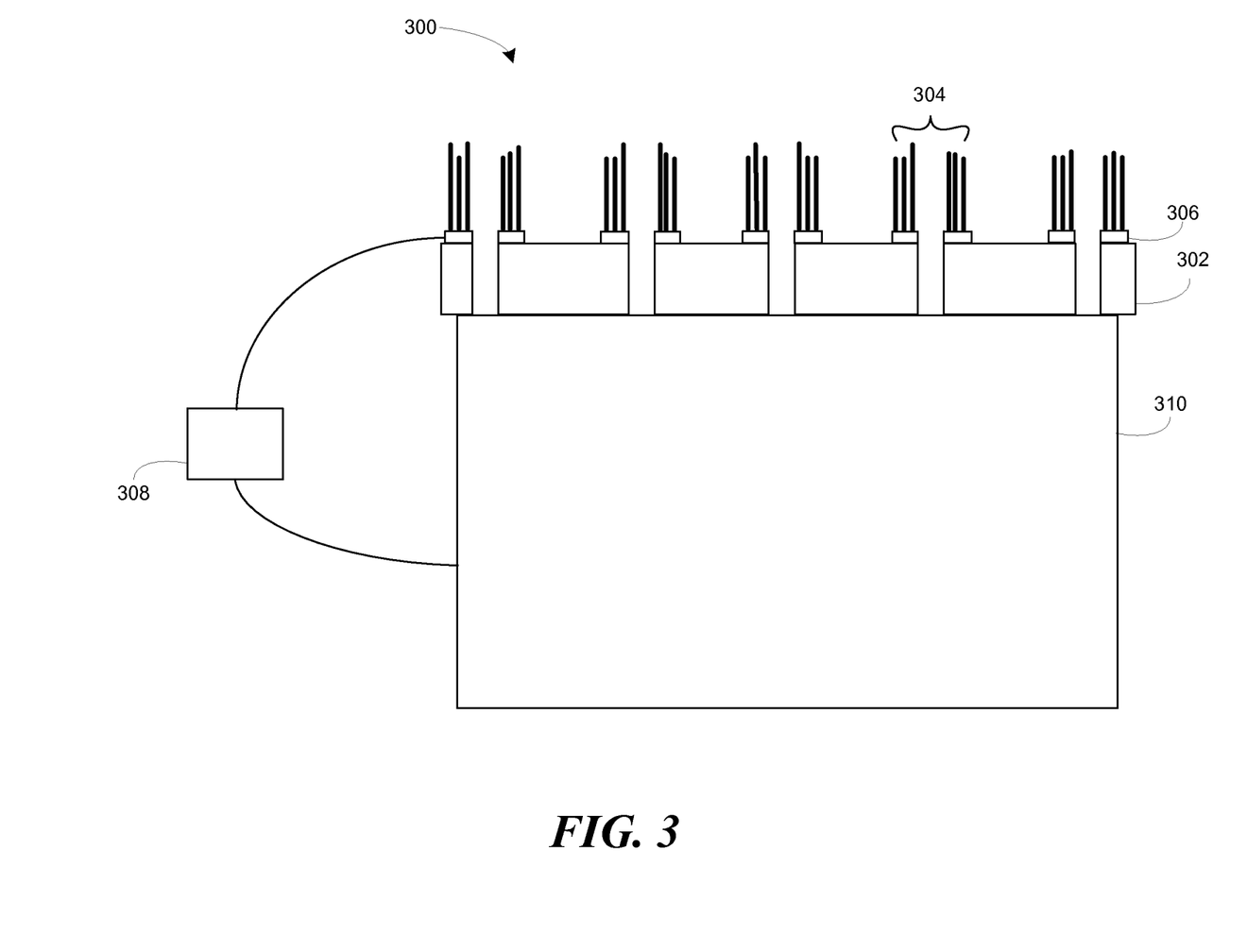
FIG. 3 is a schematic illustration of a carbon nanotube-containing active agent delivery device in accordance with some embodiments of the present invention.

An improved active agent delivery device, according to some embodiments of the present invention, is shown in FIG. 3 and is generally designated by reference numeral 300. As used herein, the term "active agent" can include, without limitation, agents for gene therapy, analgesics, antiarthritics, antiasthmatic agents, anticholinergics, anticonvulsants, antidepressants, antidiabetic agents, antidiarrheals, anesthetics, antibiotics, antigens, antihistamines, anti-infectives, anti-inflammatory agents, antimicrobial agents, antimigraine preparations, antinauseants, antineoplastics, antiparkinsonism drugs, antipruritics, antipsychotics, antipyretics, antispasmodics, anorexics, antihelminthics, antiviral agents, nucleic acids, DNA, RNA, polynucleotides, nucleosides, nucleotides, amino acids, peptides, proteins, carbohydrates, lectins, lipids, fats, fatty acids, viruses, antigens, immunogens, antibodies and fragments thereof, sera, immune stimulants, immune suppressors, sympathomimetics, xanthine derivatives, cardiovascular agents, potassium channel blockers, calcium channel blockers, beta-blockers, alpha-blockers, antiarrhythmics, antihypertensives, diuretics, antidiuretics, vasodilators comprising general, coronary, peripheral, or cerebral, central nervous system stimulants, vasoconstrictors, gases, growth factors, growth inhibitors, hormones, estradiol, steroids, progesterone and derivatives thereof, testosterone and derivatives thereof, corticosteroids, angiogenic agents, antiangeogenic agents, hypnotics, immunosuppressives, muscle relaxants, parasympatholytics, psychostimulants, sedatives, tranquilizers, ionized and non-ionized active agents, anti-fungal agents, metals, small molecules, pharmaceuticals, hemotherapeutic agents, herbicides, fertilizers, wound healing agents, indicators of change in the bio-environment, enzymes, nutrients, vitamins, minerals, coagulation factors, neurochemicals, cellular receptors, radioactive materials, cells, chemical or biological materials or compounds that induce a desired biological or pharmacological effect; and combinations thereof.

The active agent delivery device 300 includes a substrate 302 having an (i.e., at least one) aperture therein. The aperture is configured to allow an active agent to pass therethrough. Within the active agent delivery device 300, there is no limitation on the composition or material from which the substrate 102 is formed.

The active agent delivery device 300 also includes an active agent delivery member 304 disposed on a surface of the substrate 302. The active agent delivery member 304 also includes an aperture that projects in a direction perpendicular to the surface of the substrate 302 on which the active agent delivery member 304 is disposed. The aperture of the active agent delivery member 304 and the aperture of the substrate 302 are substantially coaxial. That is, within a range of about 10 percent variation, the center of the aperture in the active agent delivery member 304 is coaxial with the center of the aperture in the substrate 302.

The aperture of the active agent delivery member 304 can be different in size from the aperture of the substrate 302, with the provision that the size of the aperture in the substrate 302 must be less than or equal to the size of the aperture in the active agent delivery member 304. When more than one aperture exists in each component, the apertures can be different in size within the individual component through which they extend. Further, a single aperture can have a non-uniform size along the length of that aperture. For example, the apertures within the substrate 302 optionally can be tapered such that the apertures are larger at the top (i.e., the surface on which the active agent delivery member 304 is disposed) surface than at the bottom surface.

There is no particular limit to the shape of the apertures of the substrate 302 and/or the active agent delivery members 304. For example, an aperture can have the shape of a circle, triangle, square, rectangle, pentagon, a cross, a star, a torus or donut, any other polygon whether solid or hollow (e.g., like a donut), or any other shape.

The active agent delivery member 304 comprises a plurality of vertically aligned CNTs that project away from the substrate 302. The active agent delivery member 304 can be directly or indirectly (i.e., via an intermediate layer of material) connected to the substrate 302. The CNTs that are used to make the active agent delivery member 304 can be any type of carbon nanotube, as described above for the electrode array device 100 of FIG. 1.

There is no particular limitation on the shape of the active agent delivery member 304. When more than one active agent delivery member 304 is used, they can be identical to one another, or can have different shapes. Thus, the plurality of vertically aligned CNTs of an active agent delivery member 304 can have the shape of a circle, triangle, square, rectangle, pentagon, a cross, a star, a torus or donut, any other polygon whether solid or hollow (e.g., like donut), or any other shape.

There is no particular limitation on the height of the CNTs of the active agent delivery member 304. When more than one active agent delivery member 304 is used, they can have identical heights, or they can have different heights. For example, it may be desirable to have active agent delivery members 304 of different heights so that each active agent delivery member 304 can deliver the active agent to not only different lateral areas but different depths within the bio-environment in which the active agent delivery device 300 is implanted for in vivo applications (or to which the active agent delivery device 300 is contacted for in vitro applications).

When the pressure necessary to penetrate into a particular type of tissue is high, the CNTs can be arranged to provide the active agent delivery member 304 with a quality of "sharpness." This feature is described above with respect to the electrode array device 100 of FIG. 1. Similarly, other features of the active agent delivery members 304, including their longest lateral cross-sectional dimension, minimum spacing between individual active agent delivery members 304, and their number are similar to those for the probes 104 of electrode array device 100 of FIG. 1.

On the bottom surface (i.e., the surface opposite the one on which the active agent delivery member 304 is disposed) of the substrate 302, there is disposed an active agent chamber 310. The active agent chamber 310 can be any device or vessel that can be used to contain an active agent composition. The active agent chamber 310 includes a mechanism for regulating flow of the active agent from the active agent chamber 310 into the aperture(s) of the substrate 302 (and, by extension, into the aperture of the active agent delivery member 304). By way of example, the active agent chamber 310 can be a syringe comprising a piston and a barrel, wherein the mechanism for regulating flow or delivery of the active agent into the aperture of the substrate 302 is movement of the piston. Another active agent chamber 310 is a bottle (or other like container), wherein the mechanism for regulating flow or delivery of the active agent into the aperture of the substrate 302 is a mechanical pump. Other active agent chambers 310 can be used as would be understood by those skilled in the art to which this disclosure pertains.

The active agent delivery device 300 can further include an (i.e., at least one) optional processing component or unit 308. The optional processing component 308 is identical to the processing component 108 described for the electrode array device of FIG. 1, with the exception that it is configured to regulate the delivery of the active agent from the active agent chamber 310 to the aperture of the substrate 302.

The processing component 308 optionally can also be in electrical communication with the active agent delivery member 304 so as to facilitate delivery of the active agent. For example, a bias potential can be applied to the active agent delivery member 304 so as to induce a pumping mechanism for delivering the active agent to the desired location. That is, through an electrostatic attraction for the charged CNTs of the active agent delivery member 304, the rate at which the active agent travels through the aperture in the substrate 302 can be expedited.

Alternatively, the processing component 308 can be in electrical communication with the active agent delivery member 304 to provide the active agent delivery device 300 with all of the functionality of the electrode array device 100 of FIG. 1. In such embodiments, the overall device 300 is a combined active agent delivery device and an electrode array device. This can be accomplished by implementing electrical contacts 306, similar to those described above for the electrode array device 100 of FIG. 1.

During operation of active agent delivery device 300, the active agent delivery device 300 is implanted in, or contacted with, the bio-environment of interest. As desired, the processing component 308 can activate the mechanism for regulating flow or delivery of the active agent of the active agent chamber 310. Once the active agent is released from the active agent chamber 310, it will flow through the aperture in the substrate 302 towards the active agent delivery member 304. If the processing component 308 is in electrical communication with the active agent delivery member 304 (e.g., via an electronic contact 306), a bias voltage can be applied to the electronic contact 306 to expedite the flow of the active agent towards the active agent delivery member 304. Upon exiting the aperture of the substrate 302, the active agent can flow through the aperture of the active agent delivery member 304 to the specific area of the bio-environment in/to which the active agent delivery device 300 is implanted/contacted.

In embodiments where the active agent delivery device 300 includes all of the features of the electrode array device 100 of FIG. 1 (or the electrode array device 200 of FIG. 2), the active agent delivery device 300 also can be used measure and/or stimulate electrical activity in the particular bio-environment. In this manner, if a specific condition is detected, an appropriate active agent can be introduced to the bio-environment. The delivery of the active agent can also be accompanied by stimulation of the bio-environment.

An advantage of using a plurality of vertically aligned CNTs as the active agent delivery member 304 for the active agent delivery device 300 is that the active agent can be delivered to a larger area of the bio-environment than with existing devices. Specifically, rather than having all of the active agent be delivered to the bio-environment at the end of the active agent delivery member 304, the active agent can be delivered through gaps in the vertically aligned CNTs. Thus, the active agent can be delivered along the entire length of the active agent delivery member 304.

The active agent delivery device 300 can be fabricated by first providing a substrate 302 active agent delivery member 304 can be disposed. An aperture can be fabricated in the substrate 302. The aperture in the substrate 302 can be created by removing portions of the already-fabricated substrate 302, or it can be created by intentionally leaving a void in specified locations during fabrication of the substrate 302. Removal of portions of the substrate 302 can be achieved, for example, by micro-machining, chemical or physical etching, photolithographic techniques, or the like.

Next, if desired, the optional electrical contact 306 can be disposed on the substrate 302. This can be accomplished using any known technique for doing so. For example, the electrical contact 306 can be pre-fabricated, and can be fastened (e.g., mechanically or chemically) to the substrate 302. Alternatively, the electrical contact 306 can be fabricated directly on the substrate 302 using any known fabrication technique. Examples of such techniques are described above for the electrical contacts 106 of the electrode array device 100 of FIG. 1, with the exception that the electrical contact 306 will have an aperture therethrough.

Additionally, mechanisms for rendering the electrical contact 106 in electrical communication with the processing component 108 can also be implemented, similar to what was described above for the electrode array device 100 of FIG. 1.

After the optional electrical contact 306 has been disposed on the substrate 302, the plurality of vertically aligned CNTs can be created on the electrical contact 306. The fabrication, properties, and post-fabrication treatments of the CNTs of the active agent delivery member 304 are identical to what was described above for the electrode array device 100 of FIG. 1.

After the CNTs have been disposed on the electrical contact 306, the active agent chamber 310 can be coupled to the substrate 302. Alternatively, this can be done before any of the other steps (if desired).

Finally, the optional processing component 308 can be coupled to the active agent chamber 310 and/or the active agent delivery member 304 (via the electrical contact 306). The active agent delivery device 300 is then complete and is ready for use.

By way of example, one process for preparing an active agent delivery device 300 involves first providing a silicon wafer as the substrate 302. A thin film of $SiO_2$ is thermally grown on the top side of the substrate 302. An inductively coupled plasma reactive ion etching (ICP/RIE) instrument is used to prepare a plurality of apertures in the bottom side of the silicon wafer. The ICP/RIE instrument only etches the wafer and does not etch the $SiO_2$ film. The use of ICP/RIE allows for significantly thicker silicon wafers to be used as the substrate 302. For example, wafers having thicknesses of greater than or equal to about 250 micrometers can be used. This provides the advantage of greater mechanical stability for the active agent delivery devices 300 of the present invention.

The top surface of the substrate 302 (i.e., the one containing the $SiO_2$ film) is then patterned with a photoresist using photolithography. The pattern corresponds to the locations of the pluralities of CNTs to be grown. The pattern allow for a line-of-sight deposition path for the deposition of an Fe catalyst layer directly on the $SiO_2$ film (and the photoresist).

The photoresist and excess Fe is removed via a standard liftoff process making use of sonication in acetone. The top surface of the substrate 302, including the remaining Fe particles, is patterned with a second photoresist using photolithography. The remaining un-etched portions of the apertures in the substrate are etched using an ICP/RIE instrument. Next, the second photoresist is removed.

The CNTs are grown using catalyzed pyrolytic decomposition of hydrocarbon gases in a chemical vapor deposition chamber. In this case, the active agent delivery device 300 includes Fe catalyst particles between the pluralities of vertically aligned CNTs and the substrate 302.

In applications where electrical contacts 306 are desired, the Fe catalyst particles can serve as the electrical contacts 306.

The CNTs can be functionalized, for example, by dipping them in a solution of the functionalizing agent. If there is concern about damage to the other components of the electrode array device, then an additional photoresist layer can be created and removed to protect the other components during the functionalization step.

The bottom side of the wafer substrate 302 is glued to a flat-edged syringe, which serves as the active agent chamber 310.

At this time, the optional processing component 308 can be connected to the syringe and/or the electrical contacts 306.

Figure 4:
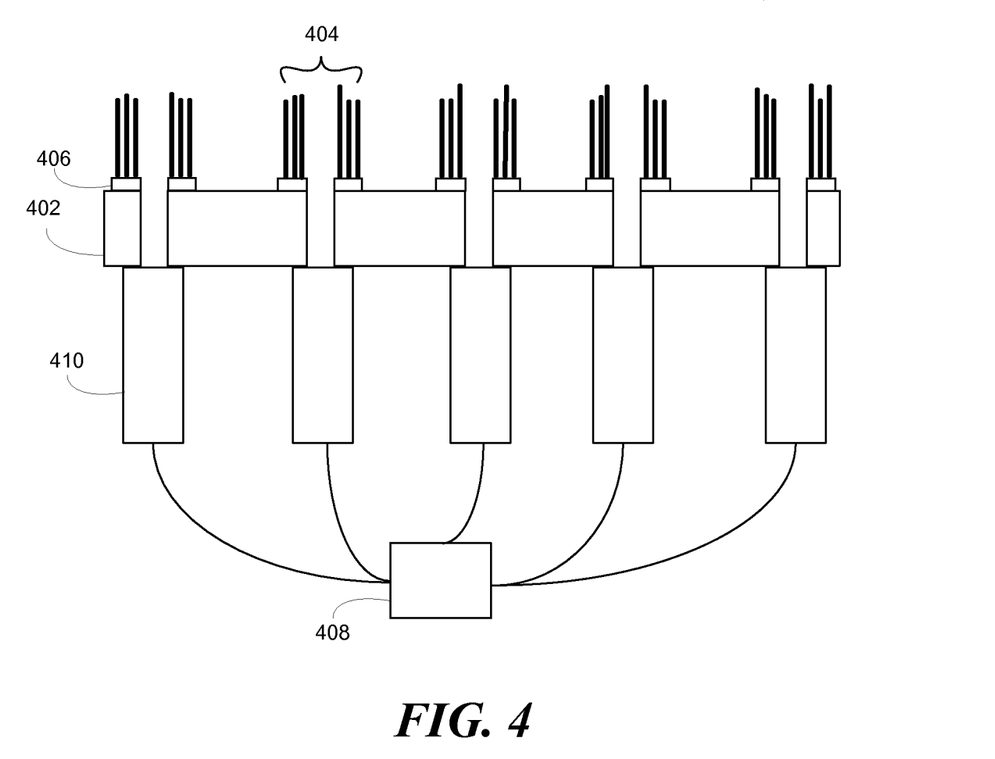
FIG. 4 is a schematic illustration of a carbon nanotube-containing active agent delivery device in accordance with other embodiments of the present invention.

Another improved active agent delivery device, according to some embodiments of the present invention, is shown in FIG. 4 and is generally designated by reference numeral 400. The active agent delivery device 400 comprises a substrate 402, an active agent delivery member 404, and an optional electrical contact 406 and processing component 408 exactly as described above for the active agent delivery device 300 of FIG. 3. The active agent chamber 410 is identical to the active agent chamber 310 of the active agent delivery device 300 of FIG. 3, with the exception that there is one active agent chamber 410 for each aperture in the substrate 402 (and, by extension, each an active agent delivery member 404).

The active agent delivery device 400 of FIG. 4 can be fabricated exactly as described for the active agent delivery device 300 of FIG. 3, with the exception that, instead of coupling a single active agent chamber 410 to all of the apertures in the substrate 402, each aperture in the substrate 402 is coupled to a separate active agent chamber 410. In addition, each active agent chamber 410 independently can be coupled to the processing component 408.

The electrode array devices 100 and 200 and the active agent delivery devices 300 and 400 disclosed herein are capable of being used in a variety of applications. For example, the electrode array devices 100 and 200 can be implemented as neural probes, cochlear implants, retinal implants, spinal cord implants, and the like. The use of vertically aligned CNTs as probes results in a size reduction, in some cases, of over 1000-fold compared to existing electrode array devices. In addition, in contrast to existing electrode array devices, the electrode array devices 100 and 200 described herein do not require a structure-providing composition or material to encapsulate the CNTs. Similarly, application of the active agent delivery devices 300 and 400 are equally limitless.

The various embodiments of the present invention are further illustrated by the following non-limiting examples.

EXAMPLES

Example 1

Fabrication of Electrode Array Devices

A thin film of $SiO_2$ was thermally grown on the top side of a silicon wafer. The top surface was then patterned with a photoresist using photolithography. The pattern corresponded to the locations of the CNTs to be grown. The pattern's apertures allowed for a line-of-sight deposition path for the deposition of an iron (Fe) catalyst layer directly on the $SiO_2$ film of the wafer. The photo-resist and excess Fe was removed via a standard liftoff process making use of sonication in acetone.

Figure 5:
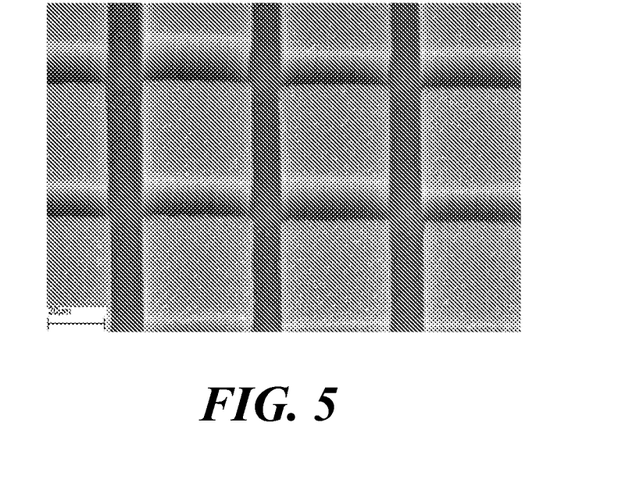
FIG. 5 is a scanning electron microscope image of an array of carbon nanotube electrodes in accordance with the data in EXAMPLE 1.

Vertically aligned CNT arrays composed of multi-walled carbon nanotubes (MWNTs) were grown via iron-catalyzed pyrolytic decomposition of hydrocarbon gases in a chemical vapor deposition (CVD) furnace. These samples were grown using a process in which the temperature in the chamber was ramped to 820 degrees Celsius (° C.) for 12 minutes under 1000 standard cubic centimeters (sccm) of argon gas, followed by a 30 minute soak with 500 sccm $H_2$, 1000 sccm $CH_4$, and 120 sccm acetylene, a 10 minute cool down period under 1000 sccm argon, and a cool to room temperature under no gas flow. A representative scanning electron microscope (SEM) image of square-shaped CNT-containing electrode arrays is shown in FIG. 5.

Some of the samples were functionalized with poly-L-lysine, laminin-1 or a combination of both. Approximately 50 microliters of the functionalizing composition were placed on the substrate surface for about 2 hours. The substrate was then washed with a phosphate buffer solution (PBS) and allowed to dry overnight. For the combined poly-L-lysine and laminin-1 functionalization of the CNTs, laminin-1 was first placed on the substrate surface for about 2 hours. The sample was then washed with PBS, and then coated with poly-L-lysine for about 2 hours. The substrate was washed with PBS, and then allowed to dry overnight.

The functionalized CNTs were more densely packed after functionalization. That is, while the untreated CNTs appeared to have the same density as when deposited on the substrate, the functionalized CNTs appeared bundled together. Thus, functionalization can be implemented to provide the CNT probes with greater mechanical strength and density.

Example 2

Characterization of the Electrode Array Devices

In order to test the mechanical compatibility of the electrode array devices of EXAMPLE 1 with brain tissue, a 0.6% agarose gel was made with an assumed stiffness of about 12 kilopascals (kPa), which corresponds to the stiffness of the brain. To make this gel, SeaPrep agarose gel was mixed with 1×PBS under constant heat. About 2 milliliters (mL) of the resulting solution was placed in several petri dishes, which were refrigerated and allowed to solidify overnight.

Once the gels solidified, a CNT array was pushed into the surface of each gel for about 1 minute, and was left implanted in the gel overnight. The CNT array was then removed from the gel and imaged via SEM to determine if the CNTs were still intact.

Figure 6A:
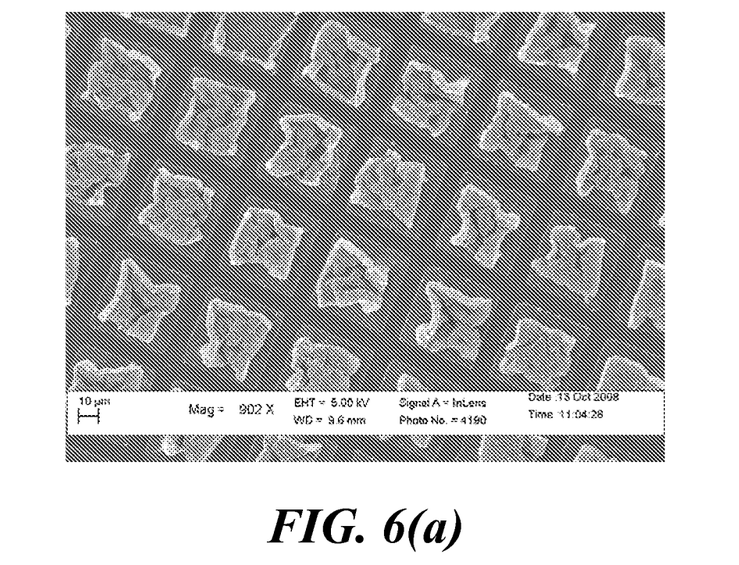
Figure 6B:
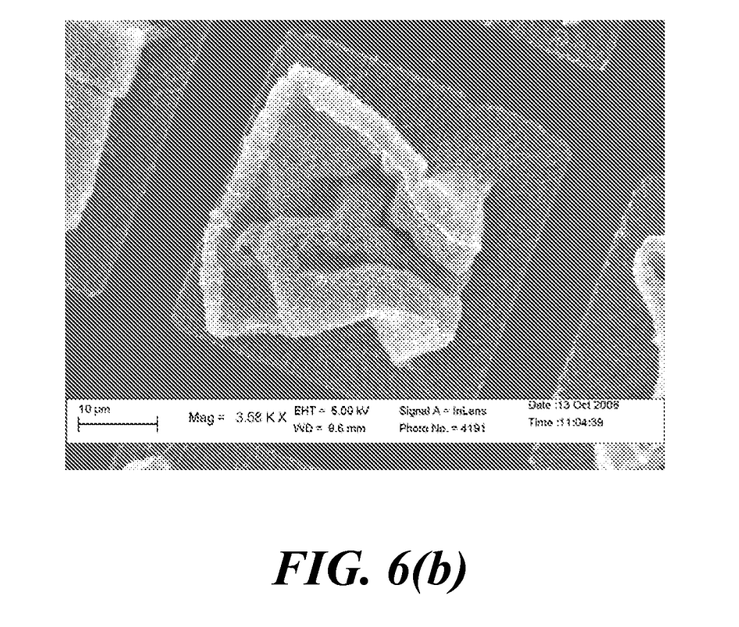
Figure 7:
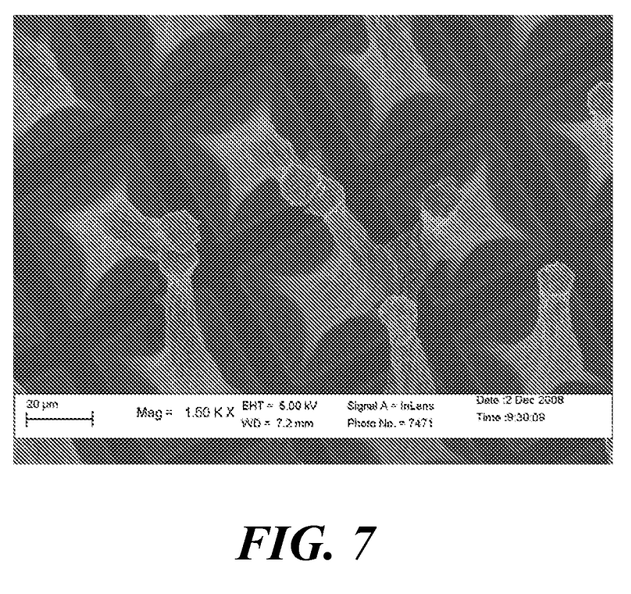
FIG. 7 is a scanning electron microscope image of an array of functionalized carbon nanotube electrodes, after implantation, in accordance with the data in EXAMPLE 2.

SEM images of the non-functionalized and functionalized CNT arrays, after removal from the gels, are provided in FIGS. 6-7. Specifically, FIG. 6(a) is a representative SEM image of a non-functionalized array of CNT electrodes after about 18 to about 24 hours of implantation in a gel. Observation at higher magnifications, as shown in the SEM image of FIG. 6(b), reveals that the nodes are reduced only minimally in vertical height. The untreated (i.e., non-functionalized) CNT electrodes were somewhat distorted in shape after implantation, but their mechanical stability and their connection to the substrate remained intact.

The SEM image of FIG. 7 illustrates a group of probes that were functionalized by both poly-L-lysine and laminin-1, after implantation in the gel. Some of the probes in the array remained vertical, while some of the probes were bent. For the most part, the probes were significantly decreased in cross sectional area, which may have been a function of the densification by functionalization and/or some damage to the CNTs in the inner region of the probes.

After removal from the gels, probes that were functionalized by poly-L-lysine had their overall structure remain intact. That is, the original vertical height and stability were retained. These results were observed uniformly across the surface of the substrate by SEM. Of the different functionalizing agents, poly-L-lysine-functionalized CNT arrays retained the greatest mechanical stability.

Figure 8:
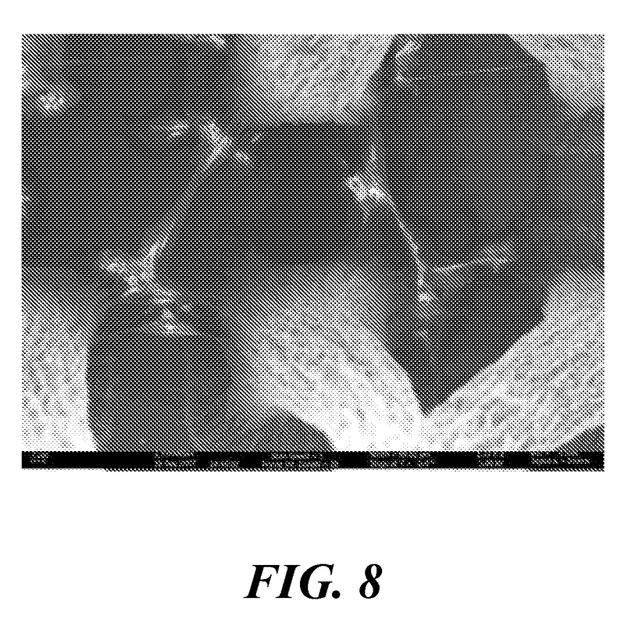
FIG. 8 is a scanning electron microscope image of an array of functionalized carbon nanotube electrodes showing cell growth in accordance with the data in EXAMPLE 2.

In addition to the mechanical studies, a cell adhesion study was performed. PC-12 cells were seeded onto the electrode arrays. Generally, the PC-12 cells attached to the CNT probes in each type of electrode array device. The samples where the CNTs were functionalized, however, had greater attachment of the PC-12 cells on the CNT arrays. A representative SEM image illustrating cell attachment between electrodes is shown in FIG. 8.

Example 3

Fabrication of an Active Agent Delivery Device

A thin film of $SiO_2$ was thermally grown on the top side of a silicon wafer. An ICP/RIE instrument was used on a silicon wafer to make a series of holes with slightly different diameters through the wafer, but not through the $SiO_2$ film. About 40 holes were spaced approximately 677 micrometers apart in the y-direction and about 2,102 micrometers apart in the x-direction. The diameter of the holes varied slightly between about 60 and about 70 micrometers, with an average diameter of 65 micrometers.

The surface of the wafer containing the $SiO_2$ film was then patterned with a photoresist using photolithography. The pattern corresponded to the locations of the CNTs to be grown. The pattern's apertures allowed for a line-of-sight deposition path for the deposition of an iron (Fe) catalyst layer directly on the $SiO_2$ film of the wafer. The photo-resist and excess Fe was removed via a standard liftoff process making use of sonication in acetone.

Figure 9A:
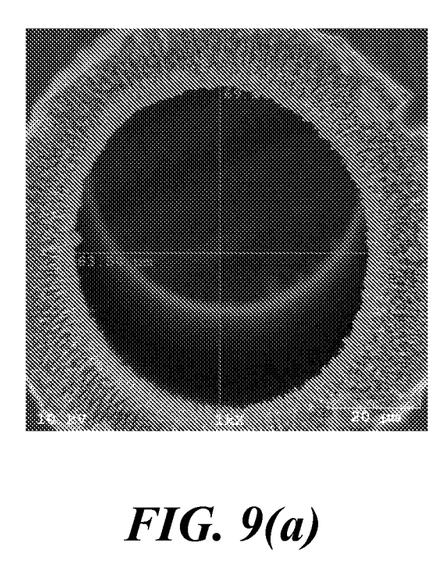

The top surface of the substrate, including the Fe particles, was patterned with a second photoresist using photolithography. The remaining un-etched portions of the apertures in the substrate were then etched using an ICP/RIE instrument. Next, the second photoresist was removed. The SEM image of FIG. 9(a) reveals a representative aperture in the wafer prior to CNT growth.

Figure 9B:
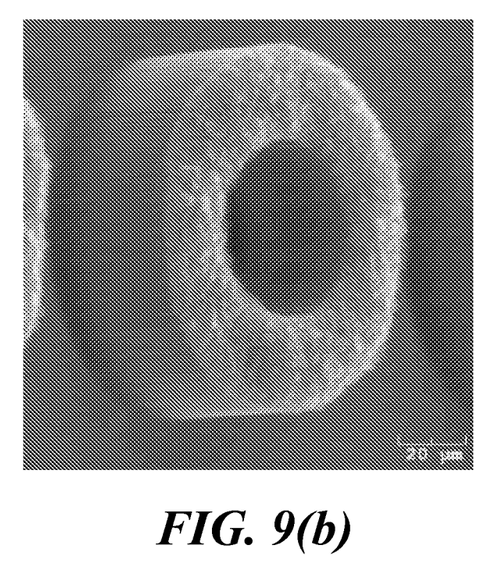

The CNTs were grown using catalyzed pyrolytic decomposition of hydrocarbon gases in a chemical vapor deposition chamber, similar to what was described in EXAMPLE 1. An SEM image of a representative active agent delivery member is shown in FIG. 9(b).

Next, the back side of the substrate (i.e., the side opposite the CNTs) was coupled with a syringe barrel.

The embodiments of the present invention are not limited to the particular formulations, process steps, and materials disclosed herein as such formulations, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of this disclosure have been described in detail with particular reference to exemplary embodiments, those skilled in the art will understand that variations and modifications can be effected within the scope of the disclosure as defined in the appended claims. Accordingly, the scope of the various embodiments of the present invention should not be limited to the above-discussed embodiments, and should only be defined by the following claims and all equivalents.

All patents and other references cited herein are incorporated by reference as if fully set forth herein.

What is claimed is:

1. An electrode array device, comprising:
   a substrate having an aperture therein; and
   a plurality of probes disposed on the substrate, wherein each probe of the plurality of probes comprises a plurality of aligned carbon nanotubes, wherein the plurality of aligned carbon nanotubes are not encapsulated by a structure-providing material, and wherein there is a gradient in a height of the carbon nanotubes such that each probe of the plurality of probes has a saw-toothed profile.

2. The electrode array device of claim 1, further comprising a plurality of electrical contacts, each of which are independently disposed between a probe of the plurality of probes and the substrate.

3. The electrode array device of claim 1, further comprising a processing component in electrical communication with at least one probe of the plurality of probes.

4. The electrode array device of claim 1, wherein each probe of the plurality of probes is electrically isolated from one another.

5. The electrode array device of claim 1, wherein the carbon nanotubes of each probe of the plurality of probes are functionalized to increase the density of the carbon nanotubes.

6. The electrode array device of claim 5, wherein the carbon nanotubes of each probe of the plurality of probes are functionalized with poly-L-lysine.

7. The electrode array device of claim 5, wherein the carbon nanotubes of each probe of the plurality of probes are functionalized with a laminin.

8. An active agent delivery device, comprising:
a substrate having an aperture therein;
an active agent delivery member disposed on a surface of the substrate and having an aperture therein, wherein the active agent delivery member comprises a plurality of aligned carbon nanotubes, wherein the plurality of aligned carbon nanotubes are not encapsulated by a structure-providing material, wherein there is a gradient in a height of the carbon nanotubes such that the active delivery agent member has a saw-toothed profile, and wherein the aperture of the active agent delivery member and the aperture of the substrate are substantially coaxial; and
means for delivering an active agent through the aperture of the substrate, the aperture of the active agent delivery member, and gaps between the aligned carbon nanotubes.

9. An active agent delivery device, comprising:
a substrate having an aperture therein;
an active agent delivery member disposed on a first surface of the substrate and having an aperture therein, wherein the active agent delivery member comprises a plurality of aligned carbon nanotubes, wherein the plurality of aligned carbon nanotubes are not encapsulated by a structure-providing material, wherein there is a gradient in a height of the carbon nanotubes such that the active delivery agent member has a saw-toothed profile, and wherein the aperture of the active agent delivery member and the aperture of the substrate are substantially coaxial; and
an active agent chamber disposed on a second surface of the substrate configured to deliver an active agent through the aperture of the substrate, the aperture of the active agent delivery member, and gaps between the aligned carbon nanotubes.

10. The active agent delivery device of claim 9, further comprising a processing component in electrical communication with the active agent chamber.

11. The active agent delivery device of claim 9, further comprising a processing component in electrical communication with the active agent delivery member.

12. The active agent delivery device of claim 9, further comprising an electrical contact, disposed between at least a portion of the active agent delivery member and at least a portion of the substrate.

13. The active agent delivery device of claim 9, wherein the plurality of aligned carbon nanotubes are functionalized to increase the density of the carbon nanotubes.

14. The active agent delivery device of claim 9, wherein the plurality of aligned carbon nanotubes are functionalized with poly-L-lysine.

15. The active agent delivery device of claim 9, wherein the plurality of aligned carbon nanotubes are functionalized with a laminin.

16. An active agent delivery device, comprising:
a substrate having a plurality of apertures therein;
a plurality of active agent delivery members disposed on a first surface of the substrate, wherein each active agent delivery member of the plurality of active agent delivery members has an aperture therein, wherein each active agent delivery member of the plurality of active agent delivery members comprises a plurality of aligned carbon nanotubes, wherein the plurality of aligned carbon nanotubes are not encapsulated by a structure-providing material, wherein there is a gradient in a height of the carbon nanotubes such that the active delivery agent member has a saw-toothed profile, and wherein each aperture of an active agent delivery member is substantially coaxial with an aperture of the substrate; and
an active agent chamber disposed on a second surface of the substrate configured to deliver an active agent through at least one aperture of the substrate, at least one active agent delivery member aperture, and gaps between the aligned carbon nanotubes of at least one active agent delivery member.

* * * * *